United States Patent
Bessard et al.

(10) Patent No.: US 6,169,183 B1
(45) Date of Patent: *Jan. 2, 2001

(54) PROCESS FOR PREPARING PYRIDINECARBOXYLIC ESTERS

(75) Inventors: Yves Bessard, Sierre; Gerhard Stucky, Brig-Glis; Jean-Paul Roduit, Grône, all of (CH)

(73) Assignee: Lonza, Ltd., Basel (CH)

( * ) Notice: Under 35 U.S.C. 154(b), the term of this patent shall be extended for 0 days.

This patent is subject to a terminal disclaimer.

(21) Appl. No.: 09/238,506

(22) Filed: Jan. 27, 1999

Related U.S. Application Data

(63) Continuation-in-part of application No. 08/893,152, filed on Jul. 15, 1997, now Pat. No. 5,925,765.

(30) Foreign Application Priority Data

Jul. 23, 1996 (CH) .................................................. 1841/96

(51) Int. Cl.$^7$ ................................................ C07D 213/30
(52) U.S. Cl. ............................................................ 546/327
(58) Field of Search ............................................. 546/327

(56) References Cited

U.S. PATENT DOCUMENTS

| | | | |
|---|---|---|---|
| 4,128,554 | 12/1978 | Heck | 544/408 |
| 4,995,902 | 2/1991 | Brunner et al. | 546/314 |
| 5,142,057 | 8/1992 | Suto et al. | 546/316 |
| 5,296,601 | 3/1994 | Suto et al. | 546/316 |
| 5,334,724 | 8/1994 | Kaufman et al. | 546/345 |

FOREIGN PATENT DOCUMENTS

| | | |
|---|---|---|
| 664754 | 3/1988 | (CH) . |
| 0282266 | 1/1990 | (EP) . |
| 0353187 | 5/1990 | (EP) . |
| 0488474 | 6/1991 | (EP) . |
| 0673932 | 9/1995 | (EP) . |
| WO 93/18005 | 9/1993 | (WO) . |

OTHER PUBLICATIONS

*Encyclopedia of Reagents for Organic Synthesis*, vol. 4, ed., L.A. Paqette, John Wiley & Sons, Chichester, (1995), 2769–2771.
Shokubai Catalysis Society of Japan, 36, (1996).
J. Mol. Cat. 66., (1991), 277.
*Chemical Abstracts, Index Guide*, 1977–1987, pp. 194$^I$ and 195$^I$.
*Nomenclature Of Inorganic Chemistry*, IUPAC, 2$^{nd}$ Ed., London, (1970), pp. 52 to 54.
Holleman/Wiberg, "Lehrbuch der anorganischen Chemie", de Gruyter, 240–241, 1985.

*Primary Examiner*—Jane Fan
(74) *Attorney, Agent, or Firm*—Fisher, Christen & Sabol

(57) ABSTRACT

A process for preparing pyridinecarboxylic esters of the general formula:

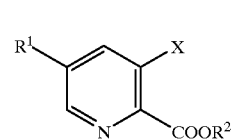

I wherein $R^1$ is hydrogen, a $C_{1-6}$-alkyl group, a $C_{1-4}$-alkoxycarbonyl group, a $C_{1-4}$-alkoxymethyl group or a fluorinated $C_{1-6}$-alkyl group, $R^2$ is a $C_{1-4}$-alkyl group and X is chlorine or bromine. The pyridinecarboxylic esters are obtained by reacing the corresponding 2,3-dihalopyridines with carbon monoxide and a $C_{1-4}$-alkanol in the presence of a weak base and a complex of palladium with a bis (diphenylphosphine). Pyridinecarboxylic esters are intermediates for preparing herbicides and drugs against fibrotic diseases.

30 Claims, No Drawings

PROCESS FOR PREPARING PYRIDINECARBOXYLIC ESTERS

This application is a continuation-in-part (c-i-p) of U.S. Ser. No. 08/893,152 (CPA), filed on Jul. 15, 1997, now U.S. Pat. No. 5,925,765.

BACKGROUND OF THE INVENTION

1. Field of the Invention

The invention relates to a process for preparing pyridinecarboxylic esters by reacting halogenated pyridines with carbon monoxide and a $C_{1-4}$-alkanol in the presence of a weak base and a catalyst. The invention further relates to a novel halopyridine as starting material for the preparation according to the invention of a novel pyridinecarboxylic ester. The pyridinecarboxylic esters preparable by the invention process have the general formula:

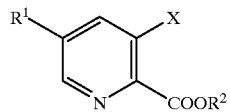

I wherein $R^1$ is hydrogen, a $C_{1-6}$-alkyl group, a $C_{1-4}$-alkoxycarbonyl group, a $C_{1-4}$-alkoxymethyl group or a fluorinated $C_{1-6}$-alkyl group, $R^2$ is a $C_{1-4}$-alkyl group and X is chlorine or bromine.

2. Background Art

Pyridinecarboxylic esters are important intermediates, for example, for preparing herbicides (European Published Patent Application No. 0488474) and for preparing drugs against fibrotic diseases (European Published Patent Application No. 0673932).

Processes for preparing pyridinecarboxylic esters by carbonylation reactions starting from mono- and dihalopyridines are known from the literature [European Published Patent Application No. 0282266; International Published Patent Application No. WO 93/18005; U.S. Pat. No. 4,128,554; and *Shokubai*, (Catalysis Society of Japan), 36, (1994), 580]. A disadvantage of these processes is that the pyridinecarboxylic esters are obtained in only moderate yields. A further disadvantage of the processes described in European Published Patent Application No. 0282266 and International Published Patent Application No. WO 93/18005 is that the dihalopyridines employed as starting material are carbonylated with low selectivity. In a further carbonylation process [*J. Mol. Cat.*, 66, (1991), 277], high yields of pyridinecarboxylic esters are obtained starting from monohalopyridines, but the reaction requires long reaction times.

BROAD DESCRIPTION OF THE INVENTION

An object of the invention is to provide an economical process for preparing selectively monocarbonylated pyridinecarboxylic esters of the general formula I in high yields starting from dihalopyridines. Other objects and advantages of the invention are set out herein or are obvious herefrom to one skilled in the art.

The objects and advantages of the invention are achieved by the method and compounds of the invention.

The invention involves a process for preparing pyridinecarboxylic esters of the general formula:

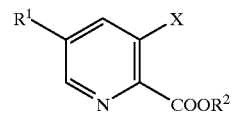

I wherein $R^1$ is hydrogen, a $C_{1-6}$-alkyl group, a $C_{1-4}$-alkoxycarbonyl group, a $C_{1-4}$-alkoxymethyl group or a fluorinated $C_{1-6}$-alkyl group, $R^2$ is a $C_{1-4}$-alkyl group and X is chlorine or bromine. In the process, 2,3-dihalopyridines of the general formula:

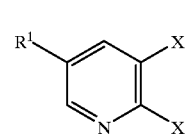

II wherein $R^1$ and X are each as defined above, are reacted with carbon monoxide and a $C_{1-4}$-alkanol in the presence of a weak base and a complex of palladium with a bis (diphenylphosphine) of the general formula:

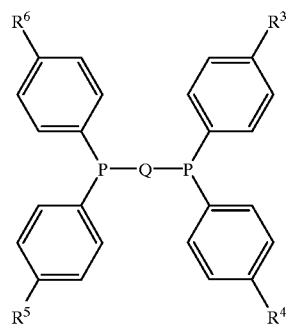

III wherein Q is a $C_{3-6}$-alkanediyl group or 1,1'-ferrocenediyl group having optionally $C_{1-4}$-alkyl- or aryl-substituted cyclopentadienyl groups and $R^3$ to $R^6$, independently of one another, are each hydrogen, $C_{1-4}$-alkyl, $C_1$-$C_4$-alkoxy, fluoromethyl, fluorine, aryl, phenoxy, nitrile or dialkylamino.

$R^1$ is hydrogen or a straight-chain or branched alkyl group having 1 to 6 carbon atoms, or an alkoxycarbonyl group having a straight-chain or branched alkyl group having 1 to 4 carbon atoms, or an alkoxymethyl group having a straight-chain or branched alkyl group having 1 to 4 carbon atoms, or a fluorinated alkyl group having a straight-chain or branched alkyl group having 1 to 4 carbon atoms. Specific examples are methyl, ethyl, n-propyl, i-propyl, n-, i- and t-butyl, pentyl and its isomers, hexyl and its isomers, methoxycarbonyl, ethoxycarbonyl, n- and i-propoxycarbonyl, n-, i- and t-butoxycarbonyl, methoxymethyl, ethoxymethyl, n- and i-propoxymethyl and n-, i- and t-butoxymethyl. Particularly preferably, $R^1$ is methoxycarbonyl, methoxymethyl or trifluoro. $R^2$ is a straight-chain or branched alkyl group having 1 to 4 carbon atoms. Examples include methyl, ethyl, n-propyl and n-, i- and t-butyl. Particularly preferably, $R^2$ is methyl or ethyl. X is chlorine or bromine; X is particularly preferably chlorine.

A 2,3-dihalopyridine of the general formula II can be prepared in a simple manner starting from 2-chloropyridine 1-oxide (U.S. Pat. No. 5,334,724) or starting from 6-hydroxynicotinic acid [Swiss Patent No. 664,754; *Encyclopedia of Reagents for Organic Synthesis*, Vol. 4, ed. L. A. Paquette, John Wiley & Sons, Chichester, (1995), 2769–2771].

The alkanol used is a straight-chain or branched aliphatic alcohol having 1 to 4 carbon atoms. Specific examples are methanol, ethanol, n- and i-propanol, and n-, i- and t-butanol. Particular preference is given to methanol and ethanol.

The reaction is carried out in the presence of a weak base. Examples of bases which are highly suitable are alkali metal acetates, alkaline earth metal acetates, alkali metal hydrogen carbonates, alkaline earth metal hydrogen carbonates, alkali metal hydrogen phosphates and alkaline earth metal hydrogen phosphates. Examples include sodium acetate, potassium acetate, magnesium acetate, calcium acetate, sodium hydrogen carbonate, potassium hydrogen carbonate, magnesium hydrogen carbonate, calcium hydrogen carbonate, disodium hydrogen phosphate, dipotassium hydrogen phosphate, magnesium hydrogen phosphate and calcium hydrogen phosphate. Sodium acetate is particularly suitable.

The catalytically active palladium bis(diphenylphosphine) complex is advantageously formed in situ by reacting a Pd(II) salt (for example, the chloride or the acetate, preferably the acetate) or a suitable Pd(II) complex, [for example, bis(triphenylphosphine)palladium(II) chloride] with the diphosphine. The palladium is preferably employed in an amount of from 0.05 to 0.4 mol percent of Pd(II), based on the halogen compound (II). The diphosphine is advantageously employed in excess (based on Pd), preferably in an amount of from 0.2 to 5 mol percent, also based on the halogen compound (II).

Use is advantageously made of bis(diphenylphosphines) (III) where Q is a straight-chain or branched alkanediyl group having 3 to 6 carbon atoms. Examples include propane-1,3-diyl, propane-1,2-diyl, butane-1,4-diyl, butane-1,3-diyl, butane-1,2-diyl, pentanediyl and its isomers and hexanediyl and its isomers. Preference is given to those compounds (III) where Q is a straight-chain alkanediyl group having 3 to 6 carbon atoms. Examples include propane-1,3-diyl, butane-1,4-diyl, pentane-1,5-diyl and hexane-1,6-diyl. Particular preference is given to 1,4-bis(diphenylphosphino)butane. Bis(diphenylphosphines) (III) where Q is a 1,1'-ferrocenediyl group having optionally $C_{1-4}$-alkyl- or aryl-substituted cyclopentadienyl groups are likewise employed advantageously. Preferred $C_{1-4}$-alkyl substituents are methyl, ethyl, n-propyl, i-propyl, and n-, i- and t-butyl, particularly preferably methyl and ethyl. Preferred aryl substituents are phenyl and optionally substituted phenyl. Substituted phenyl includes in particular groups such as p-fluorophenyl, p-methoxyphenyl, p-tolyl and p-trifluoromethylphenyl.

$R^3$ to $R^6$ of the bis(diphenylphosphines) (III) employed are each, independently of the others, hydrogen, $C_{1-4}$-alkyl, $C_{1-4}$-alkoxy, fluoromethyl, fluorine, aryl, phenoxy, nitrile or dialkylamino.

Methyl, ethyl, n-propyl, i-propyl, and n-, i- and t-butyl are advantageously employed as $C_{1-4}$-alkyl substituents, with particular preference being given to methyl and ethyl. Methoxy, ethoxy, n- and i-propoxy, and n-, i- and t-butoxy are advantageously employed as $C_{1-4}$-alkoxy substituents, with particular preference being given to methoxy and ethoxy. Phenyl and optionally substituted phenyl are advantageously employed as aryl substituents. Substituted phenyl is to be understood as meaning the above-mentioned groups. Phenoxy and optionally substituted phenoxy are advantageously employed as phenoxy substituents. Substituted phenoxy is to be understood as meaning in particular groups such as p-fluorophenoxy, p-methoxyphenoxy, benzyloxy or p-trifluoromethylphenoxy.

Preferred dialkylamino substituents are amino groups having two $C_{1-2}$-alkyl radicals. Specific examples are dimethylamino and diethylamino.

The reaction is advantageously carried out in a solvent. Suitable solvents are apolar solvents, for example, toluene or xylene, and also polar organic solvents, for example, acetonitrile, tetrahydrofuran or N,N-dimethylacetamide.

The reaction is advantageously carried out at a reaction temperature of from 100° to 250° C., preferably from 140° to 195° C. and at a carbon monoxide pressure of advantageously from 1 to 200 bar, preferably from 5 to 50 bar. After a reaction time of usually 1 to 6 hours, the compound of the general formula I is obtained in high yields. The reaction can be monitored analytically, e.g., by chromatography, and should be stopped as soon as the maximum concentration of the respective monocarbonylated product is obtained. The process according to the invention makes it possible to prepare 3-halo-5-(methoxymethyl)-2-pyridinecarboxylic esters, for example, methyl 3-chloro-5-(methoxymethyl)-2-pyridinecarboxylate, from 2,3-dichloro-5-(methoxymethyl)pyridine. 2,3-Dichloro-5-(methoxymethyl)pyridine and methyl 3-chloro-5-(methoxymethyl)-2-pyridinecarboxylate are novel.

DETAILED DESCRIPTION OF THE INVENTION

The following examples illustrate the practice of the process according to the invention.

Example 1(a)

Preparation of 2,3-dichloro-5-(methoxymethyl)pyridine

Under argon and at room temperature, 4.14 g (23 mmol) of sodium methoxide (30 percent strength solution in methanol) was added dropwise within 5 minutes to a solution of 4.11 g (20.9 mmol) of 2,3-dichloro-5-(chloromethyl)pyridine [prepared from 2,3-dichloro-5-(hydroxymethyl)pyridine by reaction with thionyl chloride] in 40 ml of methanol. The reaction mixture was subsequently heated to 60° C. for 3 hours. After the reaction had ended, the solvent was distilled off and the residue was admixed with 100 ml of water and extracted with dichloromethane (3×75 ml). The organic phase was dried over magnesium sulfate and evaporated. The yield of the product was 4.06 g (90.4 percent) of a yellow oil, purity (GC) 90.8 percent.

For analysis, the product was chromatographed over silica gel using hexane/ethyl acetate (3:1).

| $^1$H NMR(CDCl$_3$): δ = | 8.25(s, 1H); |
| --- | --- |
| | 7.78(s, 1H); |
| | 4.46(s, 2H); |
| | 3.43(s, 3H). |

MS (m/z): 192 (M+); 176; 161; 148; 124; 112.

Example 1(b)

Preparation of methyl 3-chloro-5-(methoxymethyl)-2-pyridinecarboxylate

An autoclave was charged with 1.16 g (5.6 mmol) of 2,3-dichloro-5-(methoxymethyl)pyridine, 72 mg of 1,4-bis(diphenylphosphino)butane [3 mol percent based on the 2,3-dichloro-5-(methoxymethyl)pyridine], 8 mg of bis(triphenylphosphine)palladium(II) chloride [0.2 mol percent based on the 2,3-dichloro-5-(methoxymethyl)pyridine], 1.39 g (17 mmol) of sodium acetate and 16 ml of methanol. The autoclave is repeatedly flushed with carbon monoxide to replace the air by carbon monoxide. A carbon monoxide pressure of 15 bar was then applied to the autoclave. The reaction mixture was heated to 165° C. (bath temperature) and stirred for 6 hours. After cooling to room temperature, the crude product was concentrated under reduced pressure (30 mbar), chromotographed over silica gel 60 (eluent:hexane/ethyl acetate 3:1), analyzed by gas chromatography and characterized by $^1$H NMR and MS/GC-MS. The yield of the product was 1.05 g (87 percent) of a colorless oil. Other data concerning the product was:

MS; m/z: 215 (M+); 185; 157.

| $^1$H NMR(CDCl$_3$): δ = | 8.50(s, 1H);<br>7.82(s, 1H);<br>4.53(s, 2H);<br>4.01(s, 3H);<br>3.45(s, 3H). |
|---|---|

Example 2

Preparation of methyl 3-chloro-5-(methoxymethyl)-2-pyridinecarboxylate

Example 1(b) was repeated, except that the 16 ml of methanol was replaced by 16 ml of tetrahydrofuran and 12 mmol of methanol. After a reaction time of 6 hours at a bath temperature of 195° C., 0.67 g (55 percent) of a colorless oil was obtained.

Example 3

Preparation of ethyl 3-chloro-5-(methoxymethyl)-2-pyridinecarboxylate

Example 1(b) was repeated, except that the methanol was replaced by the same volume of ethanol and the 1,4-bis(diphenylphosphino)butane was replaced by the same molar amount of 1,1'-bis(diphenylphosphino)ferrocene. After a reaction time of 2 hours at a bath temperature of 162° C., 0.54 g (47 percent) of a colorless solid was obtained. Other data concerning the product was:

MS; m/z: 229 (M+); 186; 157

| $^1$H NMR(CDCl$_3$): δ = | 8.50(s, 1H);<br>7.80(s, 1H);<br>4.51(s, 2H);<br>4.49(q, 2H);<br>3.43(s, 3H);<br>1.42(t, 3H). |
|---|---|

Example 4

Preparation of dimethyl 3-chloro-2,5-pyridinedicarboxylate

Example 2 was repeated, except that the 2,3-dichloro-5-(methoxymethyl)pyridine was replaced by the same molar amount of methyl 2,3-dichloro-5-pyridinecarboxylate. After a reaction time of 6 hours at a bath temperature of 160° C., 1.20 g (73 percent) of a yellow product was obtained. Other data concerning the product was:

m.p.: 35.5°–36° C.
MS; m/z: 229 (M+); 185; 157

| $^1$H NMR(CDCl$_3$): δ = | 9.11(s, 1H);<br>8.40(s, 1H);<br>4.05(s, 3H);<br>3.99(s, 3H). |
|---|---|

Example 5

Preparation of ethyl 3-chloro-2-pyrldinecarboxylate

Example 1(b) was repeated, except that the 1.16 g (5.6 mmol) of 2,3-dichloro-5-(methoxymethyl)pyridine was replaced by 0.76 g (5.0 mmol) of 2,3-dichloropyridine, 72 mg (0.178 mmol) of 1,4-bis(diphenylphosphino)butane was replaced by 83.2 mg (0.15 mmol) of 1,1'-bis(diphenylphosphino)ferrocene, the 8 mg (0.0112 mmol) of bis(triphenylphosphine)palladium(II) chloride was replaced by 2.2 mg (0.01 mmol) of Pd(II) acetate, the 16 ml of methanol was replaced by 14.5 ml of ethanol and the 17 mmol was replaced by 10.5 mmol of sodium acetate. After a reaction time of 1 hour at a bath temperature of 140° C., 0.83 g (88 percent) of an oily substance was obtained. Other data concerning the product was:

MS; m/z: 185 (M+); 140; 113; 85; 76

| $^1$H NMR(CDCl$_3$): δ = | 8.58(d, 1H);<br>7.81(d, 1H);<br>7.38(dd, 1H);<br>4.54(q, 2H);<br>1.44(t, 3H). |
|---|---|

Example 6

Preparation of ethyl 5-trifluoromethyl-3-chloropyridine-2-carboxylate

The reaction was carried out in a 100 ml stainless steel autoclave equipped with a magnetic stirring bar. The reagents were charged in a teflon liner in the following order: (1) ethanol (20 ml), (2) sodium acetate (1.70 g, 20 mmol), (3) 2,3-dichloro-5-trifluoromethylpyridine (2.16 g [97 percent], 10 mmol), (4)1,1'-bis(diphenylphosphino)ferrocene (166 mg, 0.30 mmol [3 mol percent]), and (5) palladium acetate (12 mg, 0.05 mmol [0.5 mol percent]). The air in the autoclave was replaced with carbon monoxide and the pressure adjusted to 15 bar. The reaction mixture was then heated to 80° C. (jacket temperature) and the reaction was carried out with stirring. After 5 hours, the reaction mixture was cooled to room temperature, filtered through celite, GC analysis indicated that the mixture consisted of 98 percent of ethyl 5-trifluoromethyl-3-chloropyridine-2-carboxylate. The mixture was concentrated under vacuum and the product was isolated by flash chromatography on silica gel eluting with ethyl acetate/hexane (1:4) affording 2.34 g (92 percent, <99 percent GC area percent). Other data concerning the product was:

| $^1$H NMR(CDCl$_3$): δ = | 8.82(1H, s);<br>8.06(1H, s);<br>4.52(2H, q):<br>1.43(3H, t). |
|---|---|

GC/MS (m/e): 254; 253 (M+); 234; 208; 181.

What is claimed is:

1. A process for preparing a pyridinecarboxylic ester of formula:

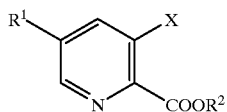

wherein $R^1$ is a fluorinated $C_{1-6}$-alkyl group, $R^2$ is a $C_{1-4}$-alkyl group and X is chlorine or bromine, consisting essentially of reacting a 2,3-dihalopyridine of formula:

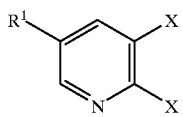

wherein $R^1$ and X are each as defined above, with carbon monoxide and a $C_{1-4}$-alkanol in the presence of a weak base and in the presence of a complex of palladium with a bis(diphenylphosphine) of formula:

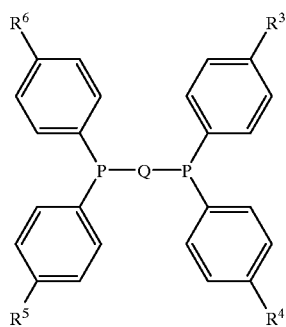

wherein Q is a $C_{3-6}$-alkanediyl group or a 1,1'-ferrocenediyl group having optionally $C_{1-4}$-alkyl- or aryl-substituted cyclopentadienyl groups and $R^3$ to $R^6$, independently of one another, are each hydrogen, $C_{1-4}$-alkyl, $C_{1-4}$-alkoxy, fluoromethyl, fluorine, aryl, phenoxy, nitrile or dialkylamino, the weak base being selected from the group consisting of an alkali metal acetate, an alkaline earth metal acetate, an alkali metal hydrogen carbonate, alkaline earth metal hydrogen carbonate, an alkali metal hydrogen phosphate, and an alkaline earth metal hydrogen phosphate, the reaction is stopped as soon as maximum concentration of the pyridinecarboxylic ester of formula I is achieved.

2. The process according to claim 1 wherein $R^1$ is a trifluoromethyl group.

3. The process according to claim 2, wherein the reaction is carried out in an apolar or polar organic solvent.

4. The process according to claim 3, wherein the palladium is employed in the form of bis(triphenylphosphine)palladium(II) chloride or palladium(II) acetate.

5. The process according to claim 4, wherein the carbon monoxide pressure is from 1 to 200 bar.

6. The process according to claim 5, wherein the reaction temperature is from 100° to 250° C.

7. The process according to claim 6, wherein the the reaction time is from 1 to 6 hours.

8. The process according to claim 1, wherein the reaction is carried out in an apolar or polar organic solvent.

9. The process according to claim 1, wherein the reaction is monitored analytically.

10. The process according to claim 1, wherein the palladium is employed in the form of bis(triphenylphosphine)palladium(II) chloride or palladium(II) acetate.

11. The process according to claim 1, wherein the carbon monoxide pressure is from 1 to 200 bar.

12. The process according to claim 1, wherein the reaction temperature is from 100° to 250° C.

13. The process according to claim 12, wherein the reaction time is from 1 to 6 hours.

14. The process according to claim 13, wherein the reaction is monitored analytically.

15. The process according to claim 14, wherein the reaction is monitored by means of chromatography.

16. A process for preparing a pyridinecarboxylic ester of formula:

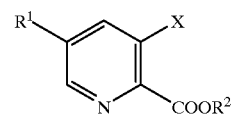

wherein $R^1$ is hydrogen, a $C_{1-6}$-alkyl group a $C_{1-4}$-alkoxycarbonyl group, or a $C_{1-4}$-alkoxymethyl group or $R^2$ is a $C_{1-4}$-alkyl group and X is chlorine or bromine, consisting essentially of reacting a 2,3-dihalopyridine of formula:

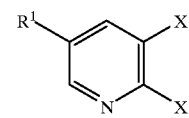

wherein $R^1$ and X are each as defined above, with carbon monoxide and a $C_{1-4}$-alkanol in the presence of a weak base and in the presence of a complex of palladium with a bis(diphenylphosphine) of formula:

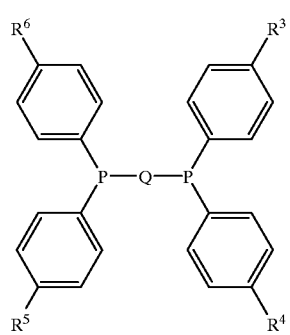

wherein Q is a $C_{3-6}$-alkanediyl group or a 1,1'-ferrocenediyl group having optionally $C_{1-4}$-alkyl- or aryl-substituted cyclopentadienyl groups and $R^3$ to $R^6$, independently of one another, are each hydrogen, $C_{1-4}$-alkyl, $C_{1-4}$-alkoxy, fluoromethyl, fluorine, aryl, phenoxy, nitrile or dialkylamino, the weak base being alkaline earth metal hydrogen carbonate, the reaction is stopped as soon as maximum concentration of the pyridinecarboxylic ester of formula I is achieved.

17. The process according to claim 16, wherein $R^1$ is a methoxycarbonyl group.

18. The process according to claim 17, wherein the reaction is carried out in an apolar or polar organic solvent.

19. The process according to claim 18, wherein the palladium is employed in the form of bis (triphenylphosophine)palladium(II) chloride or palladium (II) acetate.

20. The process according to claim 19, wherein the carbon monoxide pressure is from 1 to 200 bar.

21. The process according to claim 20, wherein the reaction temperature is from 100° to 250° C.

22. The process according to claim 21, wherein the reaction time is from one to six hours.

23. The process according to claim 16, wherein the reaction is carried out in an apolar or polar organic solvent.

24. The process according to claim 16, wherein the reaction is monitored analytically.

25. The process according to claim 16, wherein the palladium is employed in the form of bis (triphenylphosphine)palladium(II) chloride or palladium(II) acetate.

26. The process according to claim 16, wherein the carbon monoxide pressure is from 1 to 200 bar.

27. The process according to claim 16, wherein the reaction temperature is from 100° to 250° C.

28. The process according to claim 27, wherein the reaction time is from 1 to 6 hours.

29. The process according to claim 28, wherein the reaction is monitored analytically.

30. The process according to claim 29, wherein the reaction is monitored by means of chromatography.

* * * * *